United States Patent [19]
Balfour et al.

[11] Patent Number: 5,209,666
[45] Date of Patent: May 11, 1993

[54] ENDOSSEOUS IMPLANT SYSTEM WTIH CAPTURED SCREW

[75] Inventors: Alan R. Balfour, Oceanside; Donald E. Hendricks, San Diego, both of Calif.

[73] Assignee: Calcitek, Inc., Carlsbad, Calif.

[21] Appl. No.: 770,740

[22] Filed: Oct. 2, 1991

Related U.S. Application Data

[63] Continuation of Ser. No. 523,213, May 15, 1990, abandoned.

[51] Int. Cl.$^5$ .............................................. A61C 8/00
[52] U.S. Cl. ................................................... 433/173
[58] Field of Search ....................... 433/173, 174, 175

[56] References Cited

U.S. PATENT DOCUMENTS

| | | | |
|---|---|---|---|
| 4,793,808 | 12/1988 | Kirsch | 433/173 |
| 4,850,870 | 7/1989 | Lazzara et al. | 433/174 |
| 4,854,872 | 8/1989 | Detsch | 433/173 |
| 4,955,811 | 9/1990 | Lazzara et al. | 433/173 |
| 4,988,297 | 1/1991 | Lazzara et al. | 433/173 |
| 4,988,298 | 1/1991 | Lazzara et al. | 433/173 |
| 5,069,622 | 12/1991 | Rangert et al. | 433/173 |
| 5,087,200 | 2/1992 | Brajnovic et al. | 433/173 |

FOREIGN PATENT DOCUMENTS 2413883 9/1975 Fed. Rep. of Germany ...... 433/173

OTHER PUBLICATIONS

Adel, et al., "A 15 Year Study...", International Journal of Oral Surgery, vol. 10, pp. 387-416 (1981).
Jemt, "Modified Single and Short-Span Restorations...", Journal of Prosthetic Dentistry, vol. 55, No. 1, pp. 243-246 (Feb. 1986).

Primary Examiner—Cary E. O'Connor
Attorney, Agent, or Firm—John R. Merkling

[57] ABSTRACT

An endosseous dental implant system comprising an artificial root and a canted coronal section. Interposed between the artificial root and the canted coronal section is an intermediate post having a locking formation adjacent both the coronal section and the artificial root. A floating screw is captured inside the intermediate post and permits the intermediate post to be secured to the artificial root independently from the coronal section. The coronal section can be secured on the intermediate post with a free screw.

14 Claims, 2 Drawing Sheets

ENDOSSEOUS IMPLANT SYSTEM WITH CAPTURED SCREW

This is a continuation of copending application(s) Ser. No. 07/523,213 filed on May 15, 1990, now abandoned.

FIELD OF THE INVENTION

This invention relates to endosseous implants and, particularly, to dental implants.

BACKGROUND OF THE INVENTION

Successful endosseous implants date from about 1968, at which time a biocompatible metal blade was fitted into a prepared elongated receptor site. The blade itself was perforated or vented to allow bone and blood vessels to reunite readily. A projecting metal head, either unitary with or detachable from the blade, provided an anchor for attachment of a fixed bridge. Another endosseous metal implant design is the basket type having a projecting metal head. This implant is used specifically for partial support of a fixed bridge. Neither the blade nor the basket implant is designed or adapted for use as an anchor for overdentures or for use as a free-standing single tooth replacement to support a single crown.

There are at present a number of different dental implant systems in use. Most systems include an artificial root portion or implant cylinder which is placed into a custom bored hole in the jaw bone. A prosthetic coronal section is attached to the artificial root portion when healing and bone integration of the artificial root portion is complete, and a dental prosthetic appliance such as a crown, denture, partial denture or bridge is attached to the coronal section. The prosthetic coronal section must pass through the connective tissue and overlying mucosa for attachment to the prosthesis.

A problem with attachment systems is that of adjusting for undesirable placement angulation of the submerged artificial root. Since the prosthetic coronal section or post normally extends coaxially from the artificial root, and the prosthesis must be mounted on this post, undesirable angulation may make it difficult to align the prosthetic teeth with natural tooth line, particularly for a single tooth. This is a particular problem with front teeth, since for cosmetic reasons it is desirable that a screw or the like securing a crown or artificial tooth to the post does not exit through a front face of the tooth. Some attempts for adjusting angulation are provided in various existing systems, for example providing the post or prosthetic coronal section with a bendable neck portion, but this results in a weakened area which is liable to break.

Another alternative is described by Detsch in U.S. Pat. No. 4,854,872. In one embodiment, male and female prisms with hexagonal or octagonal cross-section are suggested for providing fixed, indexed positions between the artificial root and the coronal section or post. In general, the parts of the Detsch system must be set together and secured with a single screw through a coronal section and an intermediate post into the artificial root. This presents the dentist with a multiplicity of parts to be secured.

An object of our invention is to provide an indexable endosseous dental implant system with positive indexing between an artificial root and coronal post with a minimum of separable pieces.

Another object of our invention is to provide the endosseous dental implant with a relatively large number fixable indexed orientations between the artificial root and the coronal section while maintaining a relatively high resistance to torque.

It is a further object of our invention to provide such a system with multiple interlockable indexing formations wherein a first formation can be secured independently from the second formation.

These and other objects of our invention will be apparent from the following description taken with reference to the accompanying drawings.

SUMMARY OF THE INVENTION

To achieve the foregoing objects, we have invented an endosseous dental implant system comprising an artificial root and a canted coronal section. Interposed between the artificial root and the canted coronal section is an intermediate post having a locking formation adjacent both the coronal section and the artificial root. A floating screw is captured inside the intermediate post and permits the intermediate post to be secured to the artificial root independently from the coronal section. Thereafter, the coronal section can be secured on the intermediate post with a free screw.

DETAILED DESCRIPTION OF THE PREFERRED EMBODIMENT

We will now describe our preferred embodiment of our invention by reference to the accompanying drawings. Like numerals will be used to designate like parts in each of the figures.

Figure 1:
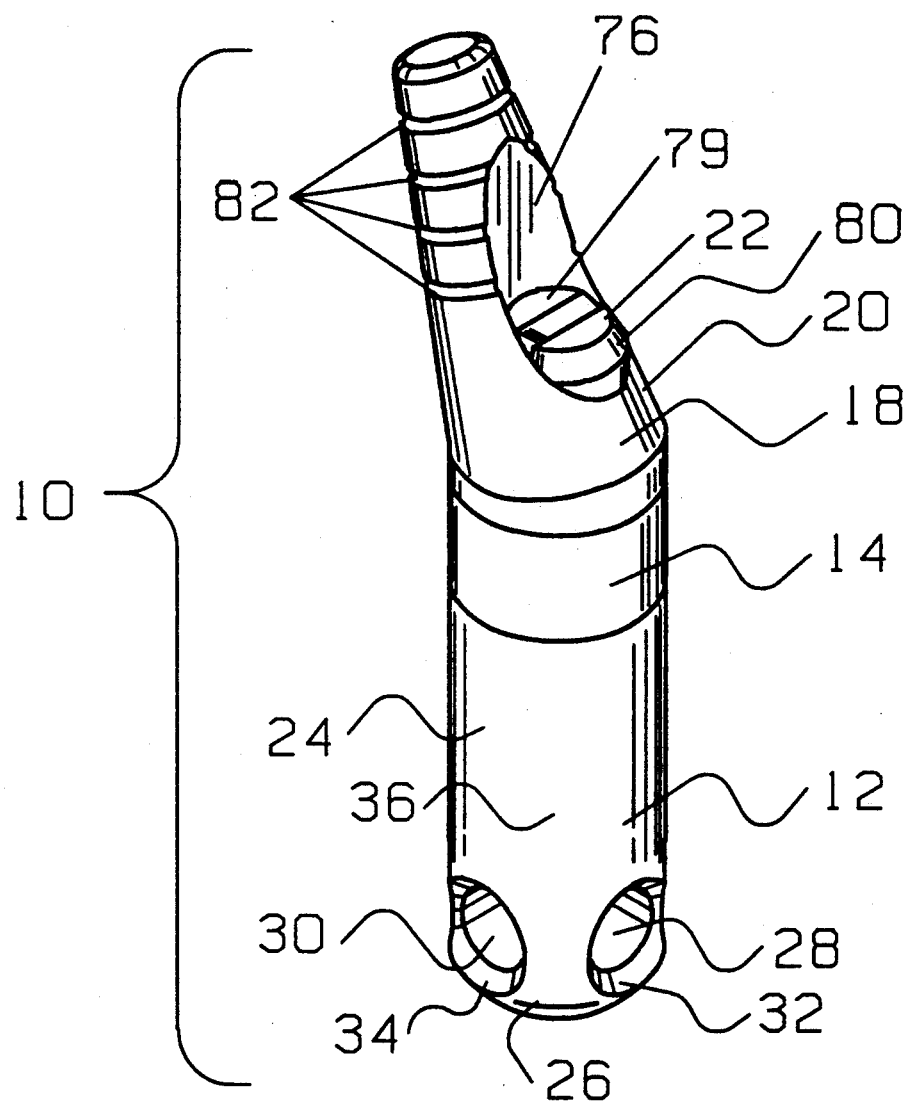
FIG. 1 is a perspective view of an endosseous dental implant system according to our present invention.

As shown in FIG. 1 an endosseous dental implant system 10, according to our present invention, comprises an artificial root 12 which can implanted into the bony structure of a patient's jaw. The artificial root 12 supports an intermediate post 14 which includes a captured or floating screw 16, shown in FIG. 2, and locking formations which we will describe more fully hereafter. On top of the intermediate post is a coronal post 18. The coronal post 18 has a canted portion 20. The canted portion 20 cooperates with the indexing formations so that the system 10 can be adjusted to compensate for any variation in placement of the implanted root 12. A free screw 22 attaches the coronal post 18 to the intermediate post 14.

The artificial root 12 comprises a generally cylindrical shaft 24 with a rounded end 26. Two orthogonal through bores 28, 30 provide areas for bony ingrowth to aide the artificial root 12 in becoming securely attached to a patient's jaw. Edges of the bores 28, 30 are countersunk 32, 34. In our preferred embodiment, an outer surface 36 of the root 12 is coated with hydroxyapatite to promote the integration of the root with the bony structure of the jaw.

Figures 2, 3:
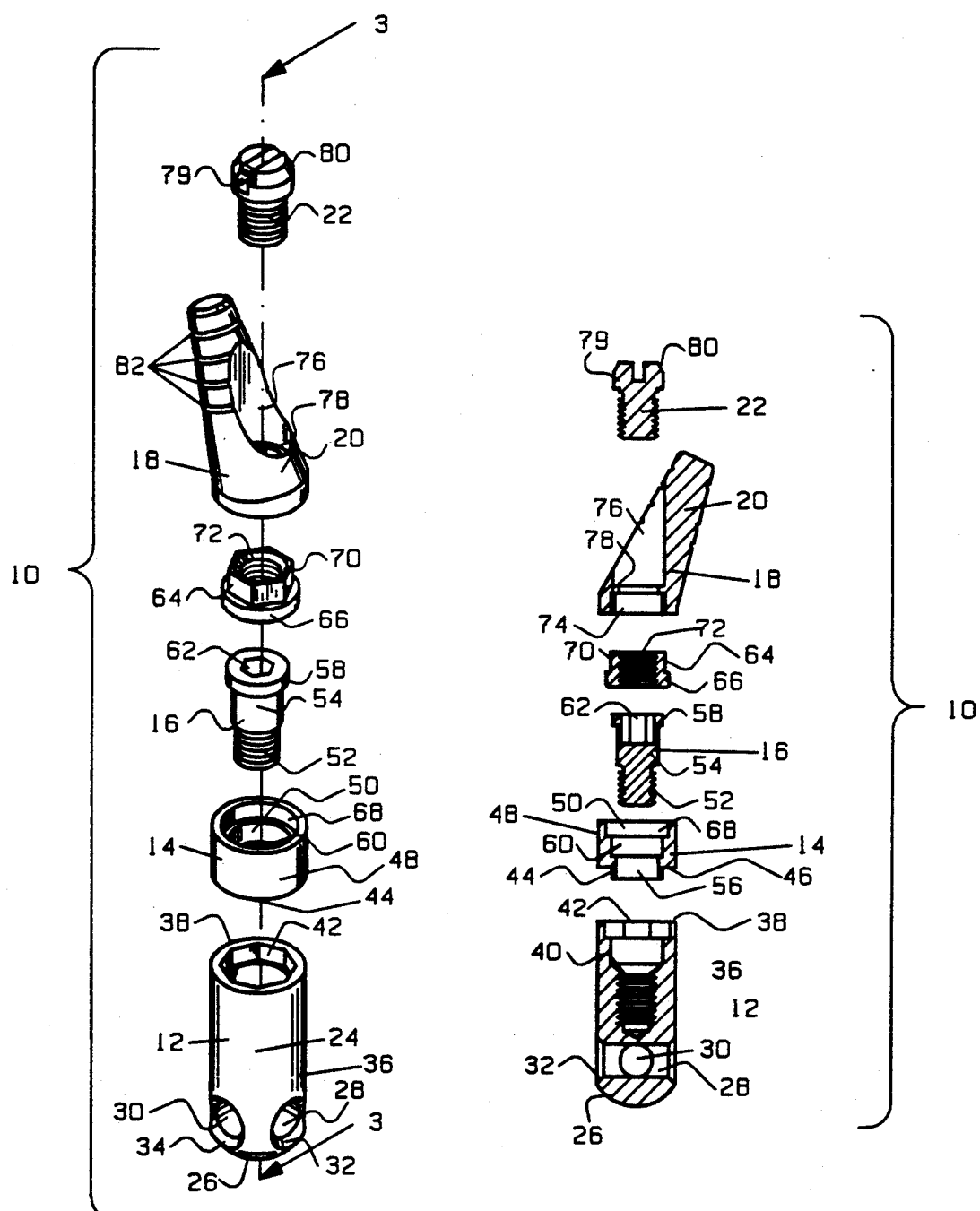
FIG. 2 is an exploded perspective view of the dental implant system of FIG. 1.
FIG. 3 is a through section of each of the components shown in FIG. 2 taken along line 3—3 of FIG. 2.

As shown in FIG. 2 and FIG. 3, at a flat upper surface 38 of the artificial root 12, there is a partially threaded bore 40. The bore 40 is coaxial with the shaft 24. Adjacent the upper surface 38 is a female octagonal recess 42 which is part of a first indexing formation.

The intermediate post 14 has a male octagonal portion 44 on a flat underside 46. The male octagonal portion 44 fits snugly into recess 42. In addition to the octagonal portion 44, the intermediate post 14 comprises a shaft 48 with a stepped coaxial bore 50. The floating screw 16 fits within the bore 50. Threads 52 on the floating screw 16 are sized to engage the partially threaded bore 40 in the root 12. The floating screw 16 also has a shaft 54 which has a greater diameter than the major diameter of the screws threads 52. This shaft 54 fits into a first portion 56 of the stepped bore 50 in the intermediate post 14. A head 58 on the screw 16 fits into a second portion 60. In our preferred embodiment, the floating screw 16 can be tightened with an allen wrench, so a hexagonal recess 62 is provided in the head 58 of the screw.

A cap 64 captures the floating screw 16 inside the intermediate post 14. This cap comprises a lip 66 which fits into a third portion 68 of the stepped bore 50. The cap is permanently secured to the intermediate post. We prefer to use electron beam welding so that no rotation will be possible. At the top of the cap is an hexagonal male insert 70 which is part of the second indexing formation. A threaded through bore 72 in the cap 64 is provided for the free screw 22. Note that the minor diameter of the threaded bore 72 must be large enough to permit the selected size of allen wrench to reach and manipulate the floating screw 16.

Note also that the relationship between the hexagonal male insert 70 and the octagonal male insert 44 should be chosen to permit as many orientations as possible to be chosen between the coronal post 18 and the artifical root 12. In the example given, the number of possible orientations would be twenty-four, or an increment of 15°. As an alternative, the hexagonal insert 70 on the cap 64 may be replaced by a cylinder or cone, particularly if a prosthesis is mounted directly on the cap, and the coronal post 18 is omitted.

The coronal post 18 fits over the hexagonal male insert 70 with an hexagonal recess 74. There is a central bore 76 above the recess 74, through which the free screw 22 can be inserted. A lip 78 in the bore 76 prevents the screw 22 from passing all the way through the coronal post 18 by engaging a head 79 on the screw. In our preferred embodiment, a slotted screw is shown, but of course alternative drive mechanisms could be used. The head 79 of the screw is chamfered 80 so that when the screw is tightened into the cap 64 the head of the screw will be effectively concealed within the canted portion 20 of the coronal post 18. Grooves 82 on the canted portion 20 are provided for securing the coronal post to a dental prosthesis.

When assembled, this embodiment of our dental implant system has only three separate parts which must be manipulated during placement on the artificial root. The intermediate post, including the cap and floating screw, is inserted on the artificial root as a single piece. The captured or floating screw can be loosened and the intermediate post oriented. Thereafter, the coronal post and free screw can be attached to the cap.

Our invention may be embodied in other specific forms without departing from the spirit or essential characteristics thereof. The present embodiment is considered in all respect to be illustrative and not restrictive, the scope of our invention being indicated by the appended claims rather than the foregoing description and all changes which come within the meaning and range of equivalency the claims are therefore intended to be embraced therein.

We claim as our invention:

1. A prosthetic dental implant attachment system for mounting a prosthetic device in fixed relationship to a jaw of a patient comprising:

a root member having an axis, a first end with securing means for securing the root member to the jaw, and a second end with first indexing means for mounting an intermediate member on said root member and for preventing angular rotation of said intermediate member about said axis, said intermediate member having a first mating indexing means on a first end of said intermediate member for cooperating with said first indexing means for preventing angular rotation of said intermediate member and for constraining said intermediate member to a discrete number of angular orientations with respect to said root member, and second indexing means on a second end of said intermediate member for mounting a coronal member and for preventing angular rotation of said coronal member about said axis, said coronal member having a second mating indexing means on a first end of said coronal member for cooperating with said second indexing means for preventing angular rotation of said coronal member and for constraining said coronal member to a discrete number of angular orientations with respect to said intermediate member and second securing means on a second end of said coronal member for securing the prosthetic device in fixed relationship thereto, said intermediate member further comprising an internal cavity, a bore into said cavity from said first end of said intermediate member and an access bore from said second end of said intermediate member into said cavity, a screw having a head captured rotatably within said internal cavity of said intermediate member and a threaded shank extending through said bore for engaging said root member, said screw being manipulable through said access bore, and means for attaching said coronal member to said intermediate member.

2. The prosthetic dental implant attachment system according to claim 1 wherein the means for attaching said coronal member comprise a screw.

3. The prosthetic dental implant attachment system according to claim 2 wherein the first indexing means comprise a recess defining a regular prism and wherein said first mating indexing means comprise a congruent regular prism.

4. The prosthetic dental implant attachment system according to claim 3 wherein the second indexing means comprise a regular prism and wherein said second mating indexing means comprise a recess defining a congruent regular prism.

5. The prosthetic dental implant attachment system according to claim 4 wherein the regular prisms of the first indexing means and the first mating indexing means are regular octagonal prisms.

6. The prosthetic dental implant attachment system according to claim 5 wherein the regular prisms of the second indexing means and the second mating indexing means are regular hexagonal prisms.

7. The prosthetic dental implant attachment system according to claim 1 wherein the first indexing means comprise a recess defining a regular prism and wherein said first mating indexing means comprise a congruent regular prism.

8. The prosthetic dental implant attachment system according to claim 7 wherein the second indexing means comprise a regular prism and wherein said second mating indexing means comprise a recess defining a congruent regular prism.

9. The prosthetic dental implant attachment system according to claim 8 wherein the regular prisms of the first indexing means and the first mating indexing means are regular octagonal prisms.

10. The prosthetic dental implant attachment system according to claim 9 wherein the regular prisms of the second indexing means and the second mating indexing means are regular hexagonal prisms.

11. A prosthetic dental implant attachment system for mounting a prosthesis in fixed relationship to a bone of a patient comprising:
- a root member having an axis, a first end having securing means for securing the root member to bone and a second end with first indexing means for mounting a second member on said root member and for preventing angular rotation of said second member about said axis,
- said second member having a first mating indexing means on a first end of said second member for cooperating with said second end of said root member for preventing angular rotation of said second member and for constraining said second member to a discrete number of angular orientations with respect to said root member, and a second end for receiving said prostheses,
- said second member further comprising an internal cavity, a bore into said internal cavity from said first end of said second member and an access bore from said second end of said second member into said cavity, and
- a screw having a head non-removably captured rotatably within said internal cavity of said of intermediate member and a threaded shank extending through said bore for engaging said root member, said captured head of said screw being manipulable through said access bore.

12. The prosthetic implant attachment system according to claim 11 wherein said indexing means on said second end of said root member comprises a recess defining a regular prism and mating indexing means on first end of said second member, said mating indexing means comprising a congruent regular prism.

13. The prosthetic implant attachment system according to claim 12 wherein the regular prisms of the indexing means and the mating indexing means are regular octagonal prisms.

14. The prosthetic implant attachment system according to claim 12 wherein the regular prisms of the indexing means and the mating indexing means are regular hexagonal prisms.

* * * * *